(12) United States Patent
Tiep

(10) Patent No.: US 7,328,703 B1
(45) Date of Patent: Feb. 12, 2008

(54) OXYGEN DELIVERY CANNULA SYSTEM THAT IMPROVES THE EFFECTIVENESS OF ALVEOLAR OXYGENATION

(76) Inventor: Brian L. Tiep, 632 Norumbega Dr., Monrovia, CA (US) 91016

( * ) Notice: Subject to any disclaimer, the term of this patent is extended or adjusted under 35 U.S.C. 154(b) by 622 days.

(21) Appl. No.: 10/924,783

(22) Filed: Aug. 25, 2004

(51) Int. Cl.
*A61M 15/08* (2006.01)
*A61M 16/00* (2006.01)
*A62B 7/00* (2006.01)
*A62B 9/02* (2006.01)
*A62B 9/00* (2006.01)
*F15C 1/08* (2006.01)

(52) U.S. Cl. ............... 128/207.18; 128/204.24; 128/204.25; 128/205.24

(58) Field of Classification Search ........... 128/203.12, 128/203.18, 203.22, 204.11, 204.12, 204.24–26, 128/205.24, 206.11, 207.18; 137/834; 138/26.3
See application file for complete search history.

(56) References Cited

U.S. PATENT DOCUMENTS

| | | | | |
|---|---|---|---|---|
| 4,054,133 A | * | 10/1977 | Myers | 128/204.26 |
| 4,535,767 A | * | 8/1985 | Tiep et al. | 128/207.18 |
| 4,572,177 A | * | 2/1986 | Tiep et al. | 128/205.17 |
| 5,666,945 A | * | 9/1997 | Davenport | 128/200.14 |
| 5,881,725 A | * | 3/1999 | Hoffman et al. | 128/204.26 |
| 6,364,161 B1 | * | 4/2002 | Pryor | 222/3 |
| 6,612,307 B2 | * | 9/2003 | Byrd | 128/204.26 |
| 6,752,152 B2 | * | 6/2004 | Gale et al. | 128/204.26 |
| 2005/0033247 A1 | * | 2/2005 | Thompson | 604/275 |

* cited by examiner

*Primary Examiner*—Danton D. DeMille
*Assistant Examiner*—Kristen C. Matter
(74) *Attorney, Agent, or Firm*—Allen A Dicke, Jr.

(57) ABSTRACT

The pulmonary oxygen flow control system delivers oxygen from a source of pressure to a nasal cannula worn by the patient. Between the source and the nasal cannula is a pendant flow structure which includes an orifice followed by a gas dynamic valve. When the downstream pressure in the cannula is high, the gas dynamic valve diverts the oxygen flow through the orifice to a flexible reservoir. Upon inhalation, the pressure at the cannula falls so that the gas dynamic valve delivers the orifice flow to the cannula and also utilizes a Venturi effect to withdraw oxygen from the reservoir and deliver it to the cannula. The cannula has nasal tubes which have angular faces and which are positioned farther into the nares to deliver the oxygen more efficiently.

20 Claims, 4 Drawing Sheets

OXYGEN DELIVERY CANNULA SYSTEM THAT IMPROVES THE EFFECTIVENESS OF ALVEOLAR OXYGENATION

FIELD OF THE INVENTION

This invention teaches a novel method of delivering oxygen to patients with severe lung disease that requires them to be prescribed supplemental oxygen. Because oxygen is delivered more efficiently, small and more portable oxygen canisters may be carried by patients on ambulatory and portable oxygen systems.

BACKGROUND OF THE INVENTION

The collective of knowledge and understanding of pulmonary rehabilitation has shown that patients with chronic lung diseases (CLD) such as chronic obstructive pulmonary disease (COPD), can live comfortable, productive and enjoyable lives if they can remain active. Patients on long-term home oxygen are limited by the portability of their system. It has been demonstrated that patients with CLD will live longer by using their oxygen continuously and that depriving them of oxygen during exertion may cause dangerous tissue hypoxia (lack of oxygen). As their impairment gradually worsens, these patients live progressively more confined existence. They find it difficult to leave their homes and gradually find themselves limited to living space of a chair or bed. This severely hurts their ability to live quality lives, and they become depressed and a burden to their families. The goal of pulmonary rehabilitation is to reverse this trend, mobilize and make these patients more active. Pulmonary rehabilitation is remarkably effective in meeting this goal.

The physiological goal of oxygen therapy is to maintain arterial oxygen saturation above 90 percent for all living conditions including wakeful rest, sleep and exertion. Because of the unique capacity for hemoglobin on the red blood cell to carry oxygen, little is gained by maintaining oxygen saturation above 90 percent, except to assure that it does not drop below 90 percent. Adding much more oxygen is wasteful and will impose an unnecessary weight burden for the patient using portable oxygen.

The Oxygen consensus

Conferences and the most recent conference of the American Thoracic Society and European Respiratory Society Standards for the Diagnosis and Treatment of COPD have emphasized the importance of maintaining an active lifestyle and the importance of a portable oxygen system.

In response to the need for mobility, coupled with the necessity for oxygen therapy in order to protect the body tissues from tissue hypoxia, there is a need to deliver oxygen to patient more efficiently. Providing adequate supplies of oxygen improves oxygen transport to the muscles, improving both strength and endurance and becoming an essential ingredient in pulmonary rehabilitation. The oxygen therapy apparatus disclosed in U.S. Pat. No. 4,572,177, co-invented by me together with Robert E. Phillips and Ben A. Otsap, teaches an oxygen conservation system. That system is very useful in the conservation of oxygen. This disclosure teaches further advancement in controlling the flow of oxygen to the patient to improve upon alveolar gas exchange and oxygen transport to the exercising muscle.

SUMMARY OF THE INVENTION

In order to aid in the understanding of this invention, it can be stated in essentially summary form that it is directed to the efficient delivery of oxygen to the patient. The system has a structure preferably in the form of a small reservoir chamber for storing oxygen during exhalation, when it is ordinarily wasted so that volume can be delivered upon the next inhalation. It includes the functions of metering, switching, storing and releasing oxygen. The system includes a nasal cannula, which receives the oxygen from the structure at an advantageous time during inhalation so that most of the oxygen effectively participates and contributes to alveolar gas exchange.

It is a purpose and advantage of this invention to provide an oxygen flow control system which includes gas dynamic switching that regulates, stores and releases oxygen to the nasal cannula, timed to the portion of the inspiratory cycle in which alveolar gas exchange takes place.

It is another purpose and advantage of this invention to provide a structure with a gas dynamic valve so that oxygen flow is diverted to storage except during the beginning of inhalation.

It is another purpose and advantage of this invention to provide an oxygen flow control system which permits a nasal cannula structure of lightweight tubing over the users ears on its way to the nasal prongs of the nasal cannula.

It is another purpose and advantage of this invention to provide an oxygen flow control system which includes an oxygen switch which switches oxygen flow to the storage reservoir inside the cannula when the cannula pressure rises to exhalation pressure and directs the oxygen flow when the cannula pressure at the nasal prongs drops to inspiratory pressure.

Other purposes and advantages of this invention will become apparent from the following description because the Summary set forth above is inherently incapable of indicating the many purposes, advantages, features and facets which are important to the invention.

DESCRIPTION OF THE PREFERRED EMBODIMENTS

Figure 1:
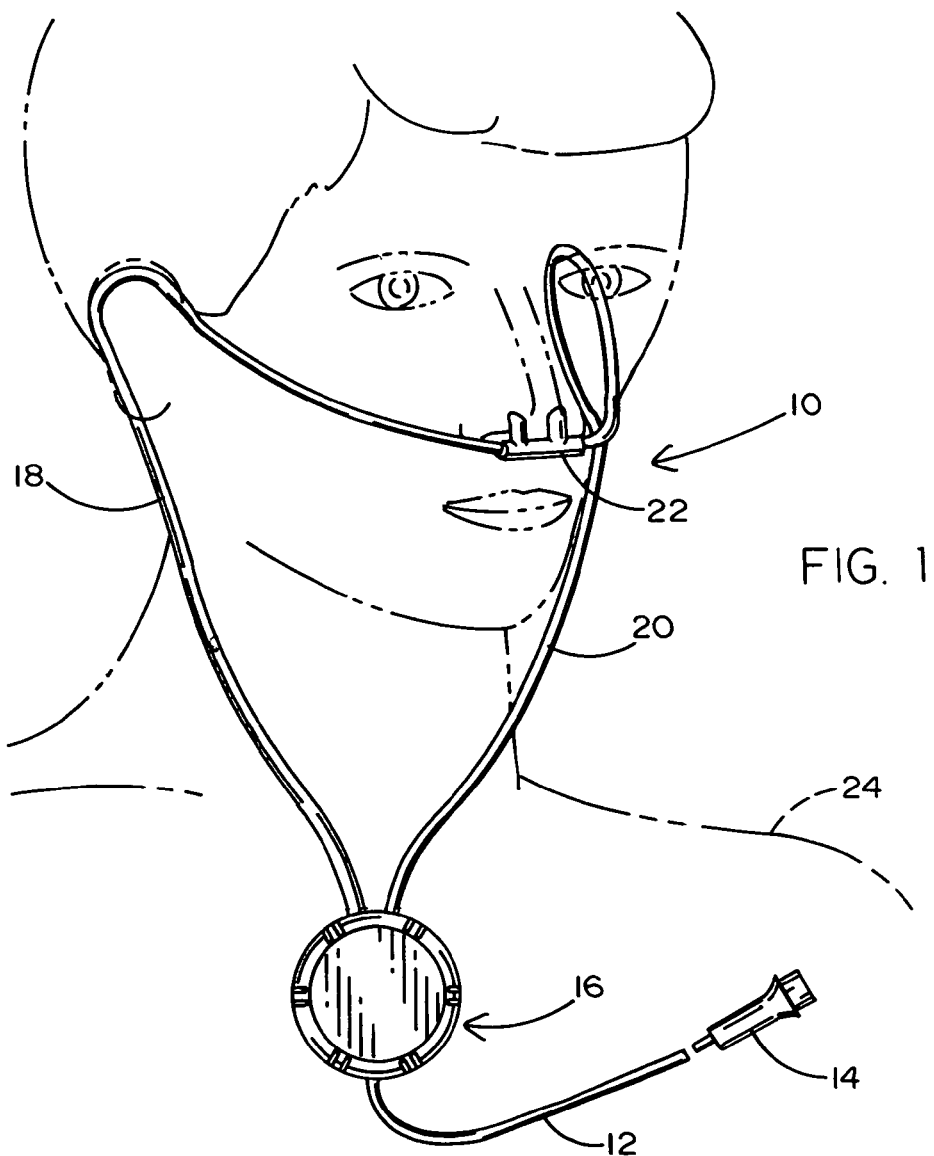
FIG. 1 is a perspective view the preferred embodiment of the oxygen delivery cannula system of this invention.
Figure 2:
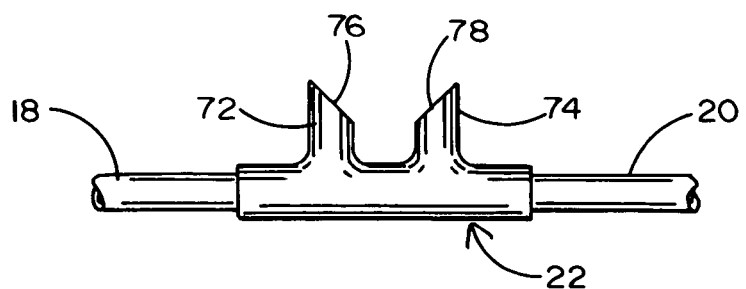
FIG. 2 is an enlarged front view of the nasal cannula with the supply tubes broken away.

The oxygen delivery cannula system of this invention is generally indicated at 10 in FIG. 1. It includes an oxygen supply tube 12 which is connected by fitting 14 to a continuous source of gaseous oxygen under pressure. The supply tube 12 is connected to pendant structure 16, the structure of which is described in detail below. Outlet tubes 18 and 20 receive oxygen from the pendant structure and are connected to the ends of nasal cannula 22. The nasal cannula 22 delivers gaseous oxygen to the patient 24, shown in dashed lines.

Figure 3:
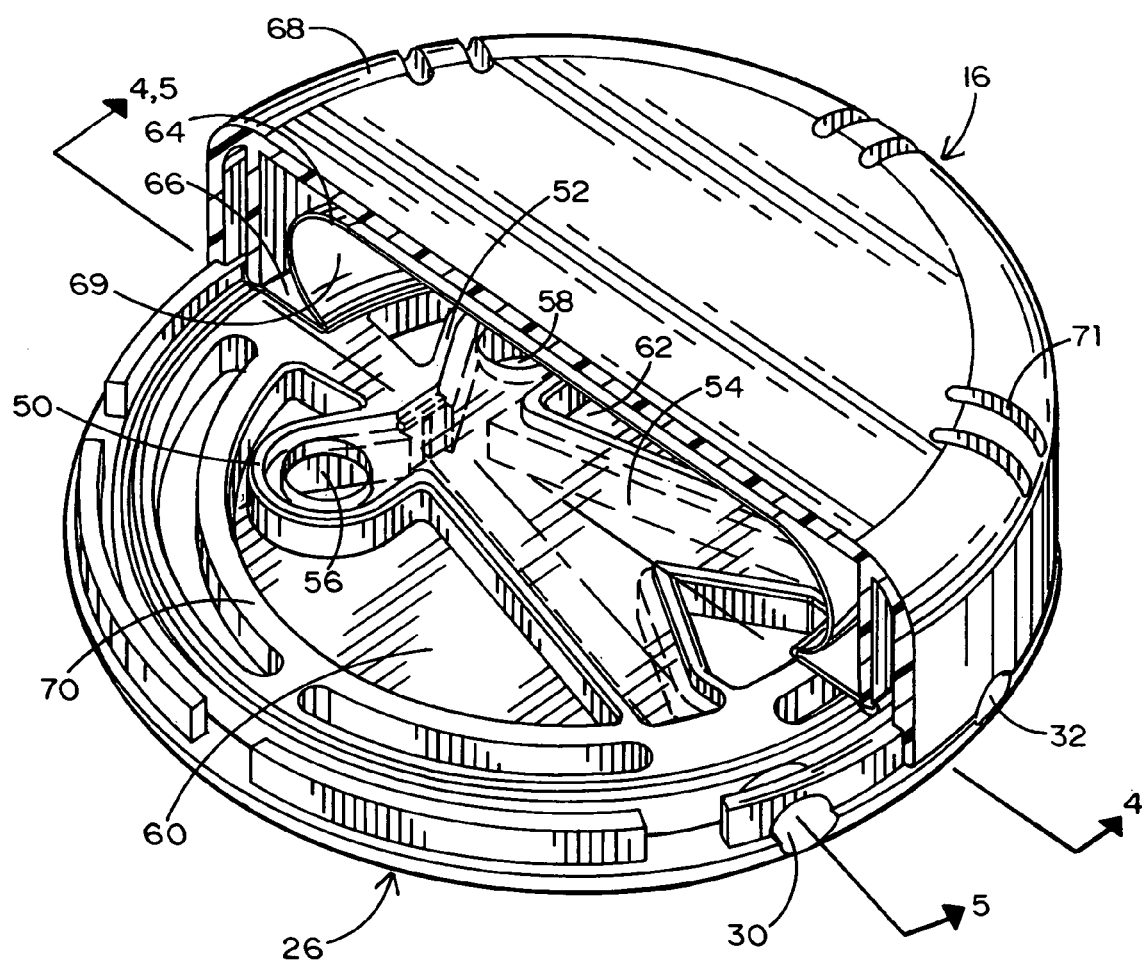
FIG. 3 is an isometric view of the pendant structure with the near half of the upper structure broken away to show the upper portion of the pendant structure in section.
Figure 4:
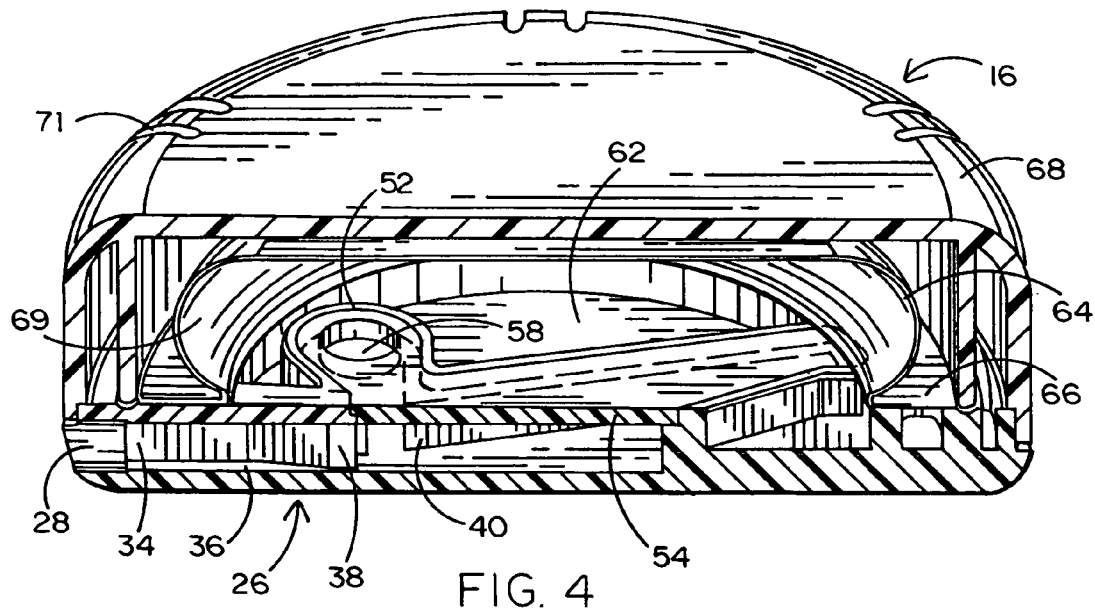
FIG. 4 is a longitudinal section through the pendant structure, as seen generally along line 4-4 of FIG. 3.
Figure 5:
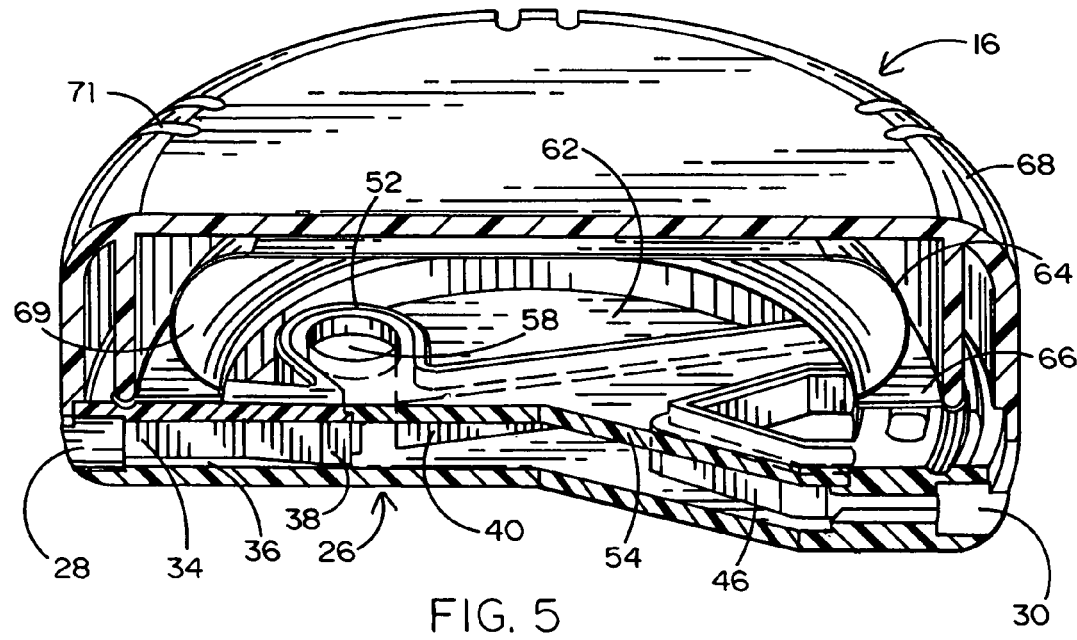
FIG. 5 is a longitudinal section taken through the pendant structure, as seen generally along line 5-5 of FIG. 3.
Figure 6:
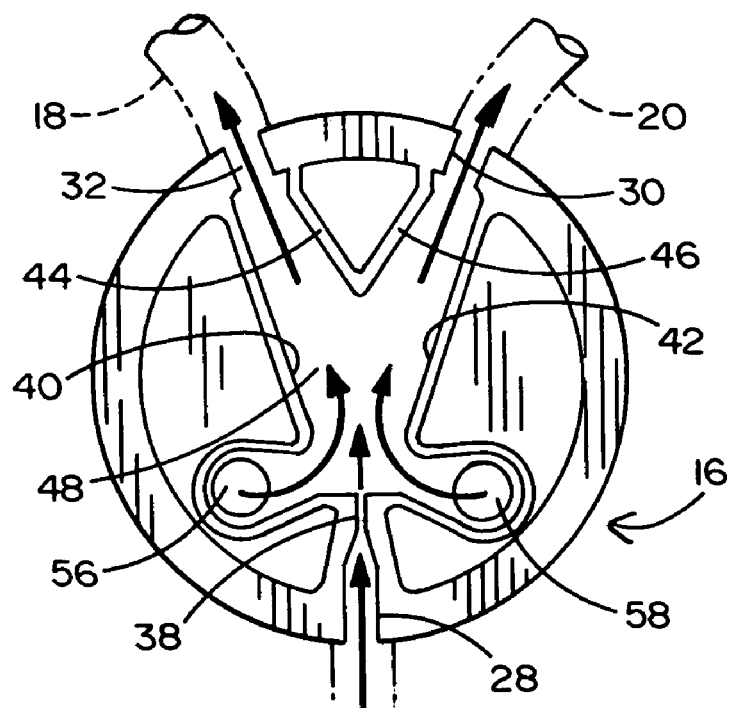
FIG. 6 is a schematic plan view showing flow during inspiration.
Figure 7:
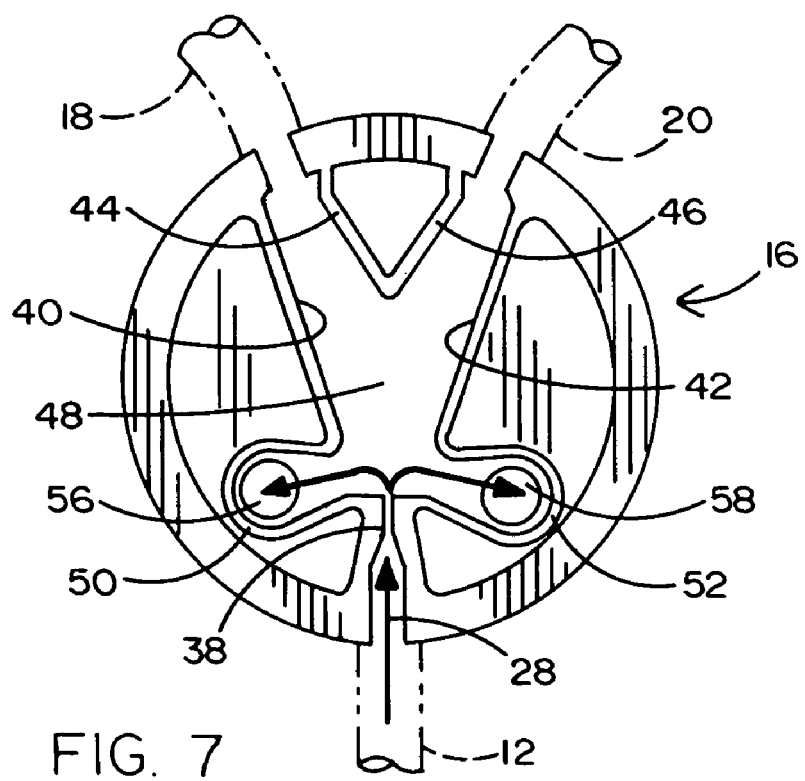
FIG. 7 is a schematic plan view showing flow during exhalation or non-flow at the cannula.

As seen in FIGS. 3, 4, and 5 the pendant structure 16 is formed of three substantially rigid parts made of injection moldable synthetic polymer composition material, and a flexible reservoir. Bottom panel 26 is the lower most panel in the pendant structure assembly. It is substantially circular in outline and is formed with a plurality of spaces and walls for various functional purposes. Its underside lies against the user's chest. Inlet opening 28 receives the supply tube 12, while outlet openings 30 and 32 receive the outlet tubes 20 and 18, respectively. Upright walls, one of which is indicated at 34 in FIGS. 4 and 5 define an inlet channel 36. These walls extend to walls which define an internal orifice slot 38. Beyond orifice slot 38, upright walls 40, 42, 44 and 46 form a Y-shaped outlet passage 48. The Y-shaped outlet passage 48 terminates in outlet openings 30 and 32. These walls are best seen in FIGS. 6 and 7. Between orifice slot 38 and Y-shaped outlet passage 48, the side walls of the flow passage are formed into right and left lobes 50 and 52. The body panel 26 thus defines the principal passages which have, at this point, open tops, so that the structure can be readily injection-molded of thermoplastic synthetic polymer composition material.

Passage cover 54 overlies the inlet channel and overlies the passages and lobes. The passage cover 54 acts to close the top of the passages except for reservoir openings 56 and 58 which are over the lobes. The passage cover 54 preferably covers only the passages to leave some reservoir spaces 60 and 62 on each side of the lobes and the Y-shaped outlet passage.

The flexible reservoir membrane 64 has a circular seal lip 66 which is clamped between body panel 28 and cover 68, see FIGS. 3, 4 and 5. The flexible material of the reservoir membrane extends inwardly from the seal lip and lies down against the top rib 70 of the body panel 26 for a short distance inward from the circular seal lip. The flexible reservoir membrane is formed in a doorknob shape, which is a figure of revolution formed with two flat walls, which terminate in a hemi-circle of revolution. The flexible material of the flexible reservoir membrane 64 is elastomeric but rolls instead of stretches so that it does not exert significant pressure on the contained gas. The reservoir membrane elastomeric material very slightly favors flow into the reservoir. The space 69 under the flexible membrane 64 and the spaces 60 and 62 form the total reservoir volume space. The doorknob shape of the flexible reservoir membrane permits it to increase and decrease in its interior volume without stretching. In order to prevent the reservoir space outside of the flexible reservoir from exerting other than atmospheric pressure on the flexible reservoir, cover 68 is vented by vent slots 71, which have sufficient opening to not limit reservoir movement.

Outlet tubes 18 and 20 are positioned in connector ports 32 and 30. The outlet tubes 18 and 20 are usually clear flexible polymer tubes and are sized to extend over the patient's ears to retain the two cannula tubes 72 and 74 in the patient's nares. The nasal cannula 22 is a one-piece structure, including the cannula tubes 72 and 74. It is preferably a polymer material and has the tubes 18 and 20 pressed therein. The length of the cannula tubes is such as to extend farther into the nares. This is possible because the cannula tubes have faces 76 and 78, which are formed at a 45 degree angle with respect to the direction of outlet oxygen through the tubular cannula and at approximately 90 degree angle with respect to each other. The angular cut provides a larger oxygen discharge area and thus a lower velocity than a square cut. This angle also distributes the oxygen toward the septum and toward the interior nasal passages.

The outlet tubes 18 and 20 can be small and flexible because they handle only oxygen. This small diameter and good flexibility permit the tube to be comfortably positioned over the patient's ears. The pendant structure 16 controls the flow of oxygen from the orifice to and from the reservoir and to the outlet tubes 18 and 20 in such a manner that oxygen is conserved as compared to continuous flow, non-conserved oxygen. Assuming that the system is full of oxygen and there is flow through the orifice 38 of about ½ liter per minute (about ¼ of standard continuous flow oxygen), the patient starts to inhale. This reduces the outlet pressure at the cannula tubes, and oxygen immediately flows into the nasal passages. Oxygen flow in the pendant structure 16 is that shown in FIGS. 6 and 7. Oxygen is present at the cannula tubes at the beginning of inhalation, at which time that oxygen is most effective because it is drawn deeply into the lungs.

At the beginning of inhalation, the entire system is full of oxygen including all the way up to the cannula outlets. Also, pressure is reduced at the cannula outlets, and oxygen flows therefrom. The orifice 38 has the reservoir openings 56 and 58 adjacent thereto so that the orifice flow acts as a Venturi to withdraw oxygen from the reservoir 69, see FIG. 6. A normal inhalation withdraws, with the help of this Venturi effect, oxygen from the reservoir. At the end of inhalation, the oxygen continues to flow from the orifice 38, but the higher back pressure at the cannula outlets at the end of inhalation defeats the jet in the gas dynamic valve structure and causes the oxygen to flow to the reservoir, as shown in FIG. 7. The reservoir fills, and then the oxygen flows through the cannula tubes 18 and 20, which are filled by oxygen flow so that oxygen is present at the cannula outlets at the beginning of the next inhalation. There is no significant exhalation into the cannula.

At the end of inhalation, the pressure builds up close to atmospheric in the tubes 18 and 20 up to the main passage 48. This buildup of pressure defeats the jet and switches the flow of oxygen from the flow paths shown in FIG. 6 to the flow shown in FIG. 7. Thus, the interior passages to the lobes 50 and 52 and the Y-shaped outlet passage 46 together with orifice 38 act as a gas dynamic valve. When the pressure in main passage 48 is about at atmospheric pressure, the flow is diverted into the reservoir through reservoir openings 56 and 58. When the pressure in main passage 48 goes below atmospheric caused by inhalation by the patient, oxygen flow into passage 48 comes from the orifice 38 and entrains flow from the reservoir 64 through reservoir openings 56 and 58, helped by venturi action. This permits an effective flow at the cannula during inhalation at a rate equivalent to 2 liters per minute of uninterrupted oxygen flow to fully supply the patient's needs, even though the actual flow rate through the orifice slot 38 is only about ½ liter per minute. During the ¾ of the time when the patient is not inhaling, the oxygen flow goes back into the reservoir. The reservoir has a volume of about 0.025 liter so that at a respiration rate of 20 breaths per minute, the ½ liter per minute oxygen flow through the orifice fills the reservoir and outlet tubes to the cannula. At the next breath, there is oxygen at the cannula.

The patient need not exhale through his nose to cause the gas dynamic valve to switch flow to the reservoir. The fact that he is no longer inhaling causes the back pressure to switch to filling the reservoir. No exhalation into the cannula or outlet tubes 18 and 20 occurs, but oxygen remains available at the cannula tubes in the nares. One advantage of this balance of pressure is that there is no need to exhale down through the outlet tubes back to the pendant to cause the pendant to switch from supply to reservoir-filling condition. This permits a smaller outlet tube which can be worn comfortable over the ear, as shown in FIG. 1.

Another advantage of not requiring exhalation into the cannula is that pursed-lip breathing can be exercised. This is a breathing condition in which exhalation is through pursed lips in order to raise the pressure in the lungs to increase the transfer of oxygen to the bloodstream. Pursed-lip breathing, as compared to regular breathing, can increase blood oxygen content in the order of 10 percentage points. This breathing method causes hyperinflation, increases oxygenation and breathing efficiency and reduces breathlessness.

This invention has been described in its presently preferred embodiment, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A pulmonary oxygen flow control system comprising:
    a structure, said structure having an oxygen inlet connection and an outlet connection, an inlet passage in such structure connected to said inlet connection, said inlet passage terminating in a venturi orifice, an outlet passage in said structure, said outlet passage being positioned in the flow path of said venturi orifice to receive oxygen flowing through said venturi orifice, a reservoir passage adjoining said outlet passage and lying adjacent said venturi orifice, a reservoir connected to said reservoir passage;
    a nasal cannula connected to said outlet passage;
    said venturi orifice, said outlet passage and said reservoir passage being configured so that when a patient is inhaling from said nasal cannula, oxygen flows through said venturi orifice and draws oxygen from said reservoir because of low pressure in said outlet passage due to venturi caused decrease in pressure with oxygen flow delivered to said cannula, and when the patient is not inhaling, oxygen is directed from said orifice into said reservoir passage and into said reservoir due to increased pressure in said outlet passage so that said passages act as a gas dynamic valve directing oxygen flow to deliver at the very beginning of inhalation and to permit pursed lip breathing.

2. The pulmonary oxygen control system of claim 1 wherein said reservoir, said outlet passages and said cannula tubes have a volume of about 25 milliliters so that oxygen flow through said orifice fills said reservoir and fills said outlet passages and cannula tubes before the next inhalation.

3. The pulmonary oxygen control system of claim 1 wherein said reservoir comprises a reservoir chamber connected to said reservoir passage and a flexible reservoir membrane within said reservoir chamber to form a reservoir which contains oxygen passing through said reservoir opening, said flexible reservoir membrane being configured to favor flow into said reservoir so that exhalation into said nasal cannula is not necessary to cause oxygen flow into said reservoir.

4. The pulmonary oxygen control system of claim 3 wherein said reservoir chamber is vented so that said flexible reservoir membrane can expand and contract the reservoir by rolling its membrane walls within said reservoir chamber.

5. The pulmonary oxygen control system of claim 1 wherein said outlet passage is a first outlet passage and there is a second outlet passage, and wherein said reservoir passage is a first reservoir passage and there is a second reservoir passage adjacent said venturi orifice, said first and second reservoir passages being respectively adjacent to said first and second outlet passages so that said venturi orifice and said passages act as a fluid dynamic valve which selectively delivers oxygen from said venturi orifice and from said reservoir to said outlet passages or delivers oxygen from said venturi orifice to said reservoir until said reservoir is filled and thereupon delivers oxygen to said outlet passages and said cannula to fill said cannula.

6. The pulmonary oxygen control system of claim 5 wherein said cannula has first and second cannula tubes for extending into the patients nares, said cannula tubes each having a tubular axis and terminating in surfaces which are formed at an acute angle to the tubular axis so that they partially face each other to provide an outlet area larger than the cross sectional area of said cannula tube.

7. A pulmonary oxygen flow control system comprising:
    a structure, said structure having a body panel, said body panel having an oxygen inlet connection and an outlet connection, an inlet passage in said body panel connected to said inlet connection, said inlet passage terminating in an venturi orifice, an outlet passage in said body panel, said outlet passage being positioned in the flow path of said venturi orifice to receive oxygen flowing through said venturi orifice, a reservoir passage in said body panel adjoining said outlet passage and lying in the low pressure zone adjacent said venturi orifice;
    a passage cover overlying said body panel to cover said passages, said body panel and said passage cover defining said inlet passage, said outlet passage and said reservoir passage;
    a reservoir cover, a flexible reservoir mounted on said panel body and secured on said body panel by said reservoir cover, said passage cover having a reservoir opening therethrough into said flexible reservoir from said reservoir passage;
    said outlet passage being configured to be connected to a nasal cannula;
    said venturi orifice, said outlet passage and said reservoir passage being configured so that when a patient is inhaling from the nasal cannula, oxygen flows through said venturi orifice and draws oxygen from said reservoir because of low pressure in said outlet passage due to venturi caused decrease in pressure with oxygen flow delivered to said cannula, and when the patient is not inhaling, oxygen is directed from said orifice into said reservoir passage and into said reservoir due to increased pressure in said outlet passage so that said passages act as a gas dynamic valve directing oxygen flow.

8. The pulmonary oxygen control system of claim 7 wherein said reservoir cover is a vented cover over said flexible reservoir to constrain said flexible reservoir.

9. The pulmonary oxygen control system of claim 7 wherein there are first and second reservoir openings and first and second outlet passages.

10. The pulmonary oxygen control system of claim 7 wherein there is a midline through said structure and said orifice lies on said midline and said outlet passages comprise first and second outlet passages in said structure and walls to define a Y-shaped outlet, said passages lying substantially equidistant on the opposite sides of said midline and said reservoir passages comprise first and second reservoir passages adjacent said orifice, each of said first and second reservoir passages lying opposite said midline.

11. The pulmonary oxygen control system of claim 10 wherein said first outlet passage and said first reservoir passage intersect each other at a point on one side of said midline and said second outlet passage and said second reservoir passage intersect each other at a point on the other side of said midline.

12. The pulmonary oxygen control system of claim 11 wherein said first and second outlet passages in said structure join each other adjacent said reservoir passages to form a Y-shaped outlet passage adjoining said reservoir passages, said Y-shaped outlet passage lying on said midline.

13. A pulmonary oxygen flow control system comprising:
a structure, said structure having a body panel, said body panel having an oxygen inlet connection and an outlet connection, an inlet passage in said body panel connected to said inlet connection, said inlet passage terminating in a venturi orifice, an outlet passage in said body panel, said outlet passage being positioned in the flow path of said venturi orifice to receive oxygen flowing through said venturi orifice, a reservoir passage in said body panel adjoining said outlet passage and lying in the low pressure zone adjacent said venturi orifice;
a passage cover overlying said body panel to cover said passages, said body panel and said passage cover defining said inlet passage, said outlet passage and said reservoir passage;
a reservoir cover, a flexible reservoir membrane mounted on said panel body and secured on said body panel by said reservoir cover to define a reservoir, said passage cover having a reservoir opening therethrough into said reservoir from said reservoir passage;
said outlet passage being configured to be connected to a nasal cannula, a nasal cannula connected to said outlet passage, said nasal cannula having first and second inlet tubes connected to said outlet passage of said structure and said cannula having first and second cannula tubes extending therefrom, said cannula tubes being sized and positioned with respect to each other to extend into the patient's nares, said cannula tubes having faces which are angular with respect to the centerline of said cannula tubes so that said faces partially face each other to direct oxygen toward the patient's septum, to provide a discharge interface area larger than cannula tube area;
said venturi orifice, said outlet passage and said reservoir passage being configured so that when a patient is inhaling from said nasal cannula, oxygen flows through said venturi orifice and draws oxygen from said reservoir because of low pressure in said outlet passage due to venturi caused decrease in pressure with oxygen flow delivered to said cannula, and when the patient is not inhaling, oxygen is directed from said orifice into said reservoir passage and into said reservoir due to increased pressure in said outlet passage so that said passages act as a gas dynamic valve directing oxygen flow.

14. The pulmonary oxygen control system of claim 13 wherein said cannula tubes are sized for flow only from said cannula so that said cannula tubes are sufficiently small that they can be worn comfortably over the ears.

15. A pulmonary oxygen control system comprising:
a structure, said structure having an inlet passage, an venturi orifice, a main passage and a nasal cannula connector in serial connection, said inlet passage, said venturi orifice and said main passage being in line with each other and defining a substantially straight flow path, said venturi orifice being sized to pass gaseous oxygen at about one liter per minute to supply the oxygen needs of a patient and to reduce pressure in said main passage when said nasal cannula connector is below atmospheric pressure;
said structure having first and second reservoir passages therein and a reservoir recess in said structure, said first and second reservoir passages lying on first and second opposite sides of said flow path in said main passage adjacent the outlet of said venturi orifice, said first and second reservoir passages intersecting said main passage adjacent said venturi orifice to form a gas dynamic valve so that when pressure in said main passage is at atmospheric pressure, flow from said orifice goes into said reservoir passages and said reservoir recess, and when the pressure in said main passage is below atmospheric pressure flow from said orifice and flow from said reservoir goes through said main passage to said nasal cannula connector;
a nasal cannula connected to nasal cannula connector in serial connection to said main passage so that pressure in said nasal cannula controls directional flow through said gas dynamic valve.

16. The pulmonary oxygen control system of claim 15 wherein there is a reservoir with flexible walls within said recess so that said reservoir expands and contracts with oxygen flow through said reservoir passages, said flexible walls being resilient and configured to favor flow into said reservoir.

17. The pulmonary oxygen control system of claim 16 wherein said flexible reservoir has a variable volume of about 0.025 liter so that said reservoir fills and continued oxygen flow through said orifice fills said cannula so that oxygen is available at said cannula at the beginning of each inhalation.

18. The pulmonary oxygen control system of claim 15 wherein said main passage divides into a Y-shaped outlet passage which becomes first and second cannula passages downstream of said venturi orifice and downstream of said reservoir passages and there are first and second outlet tubes connected to said cannula passages, said tubes being connected to said cannula and being sufficiently small and flexible to be worn over the patient's ears.

19. The pulmonary oxygen control system of claim 18 wherein said cannula has first and second cannula tubes, said tubes being sized to extend into the patient's nares, said cannula tubes having axes and having faces at an acute angle with respect to said tube axes so that said faces are partially directed toward each other when said axes are parallel to increase the tube exit area interface.

20. The pulmonary oxygen control system of claim 15 wherein said structure is made up of a plurality of layers of injection-moldable synthetic polymer composition and is sized so that it can be worn as a pendant to minimize the length of the oxygen tube between said structure and said cannula.

* * * * *